US00H002056H

(19) United States

(12) Statutory Invention Registration

Schmidt et al.

(10) Reg. No.: US H2056 H

(43) Published: Dec. 3, 2002

(54) MODEL FOR VON HIPPEL-LINDAU DISEASE

(75) Inventors: Laura S. Schmidt, Mt. Airy, MD (US); Wenbin Ma, Frederick, MD (US); Lino Tessarollo, Frederick, MD (US); Berton Zbar, Garrett Park, MD (US)

(73) Assignee: The United States of America as represented by the Department of Health and Human Services, Washington, DC (US)

(21) Appl. No.: 09/971,476

(22) Filed: Oct. 4, 2001

(51) Int. Cl.[7] ..... C07H 21/04; C12N 9/00; C12N 5/00

(52) U.S. Cl. ..... 536/23.1; 435/183; 435/325

(58) Field of Search ..... 536/23.1; 435/325, 435/183

(56) References Cited

PUBLICATIONS

Carmeliet et al. (Cell 1999 Jul. 23; 98(2):147–157).*

Hasse et al. (PNAS 2001 Feb. 13; 98(4):1583–1588).*

* cited by examiner

*Primary Examiner*—Michael J. Carone

*Assistant Examiner*—Aileen J. Baker

(74) *Attorney, Agent, or Firm*—Klarquist Sparkman, LLP

(57) ABSTRACT

Disclosed herein are nucleic acid molecules that can be used to effect a loss of function of the von Hippel-Lindau (VHL) allele in somatic and/or germ cells of a mammal and methods for using these molecules to create conditional VHL gene targeted and conditional VHL knockout animals. Disclosed herein are conditional VHL gene target vectors which, when inserted into an endogenous VHL gene, can result in deletion of an exon of a VHL gene by site-specific recombinaton when a recombinase is expressed conditionally.

1 Claim, 7 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

A schematic of the VHL gene target construct in pBluescript vector

Fig. 1: A schematic of the VHL gene target construct in pBluescript vector
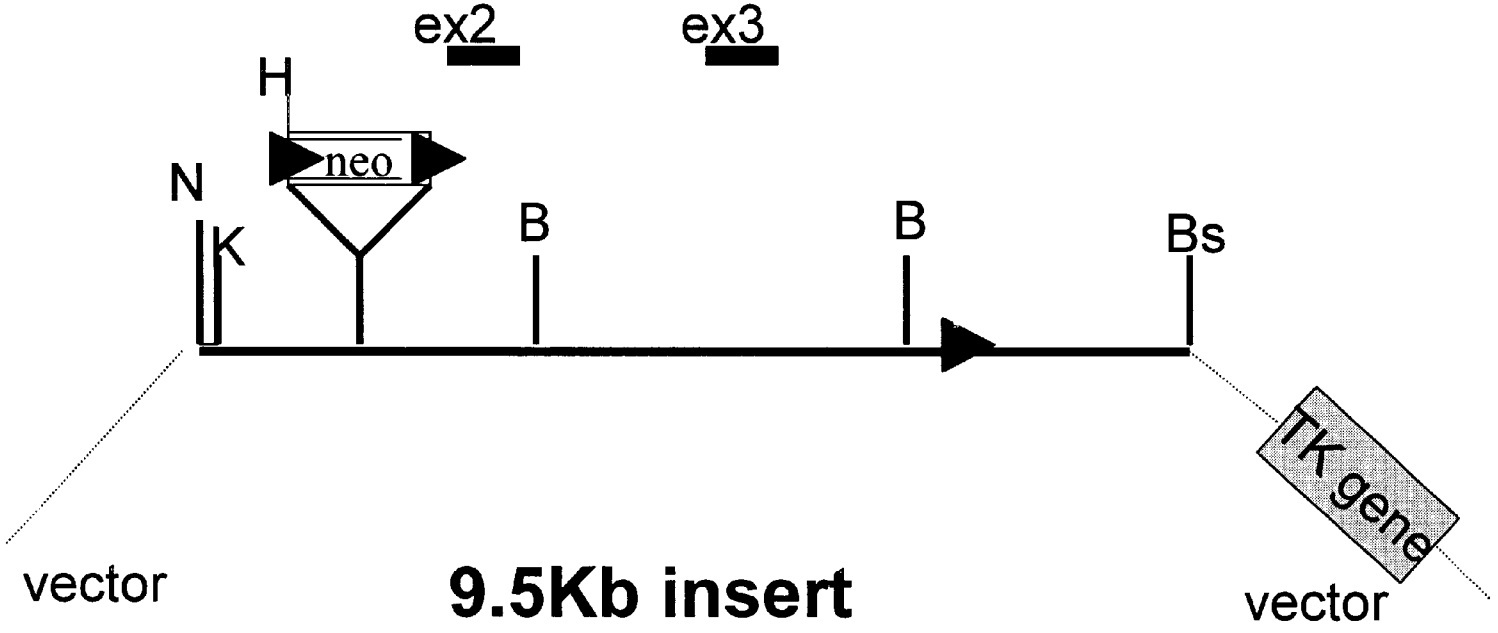

Fig. 2: VHL wild-type allele
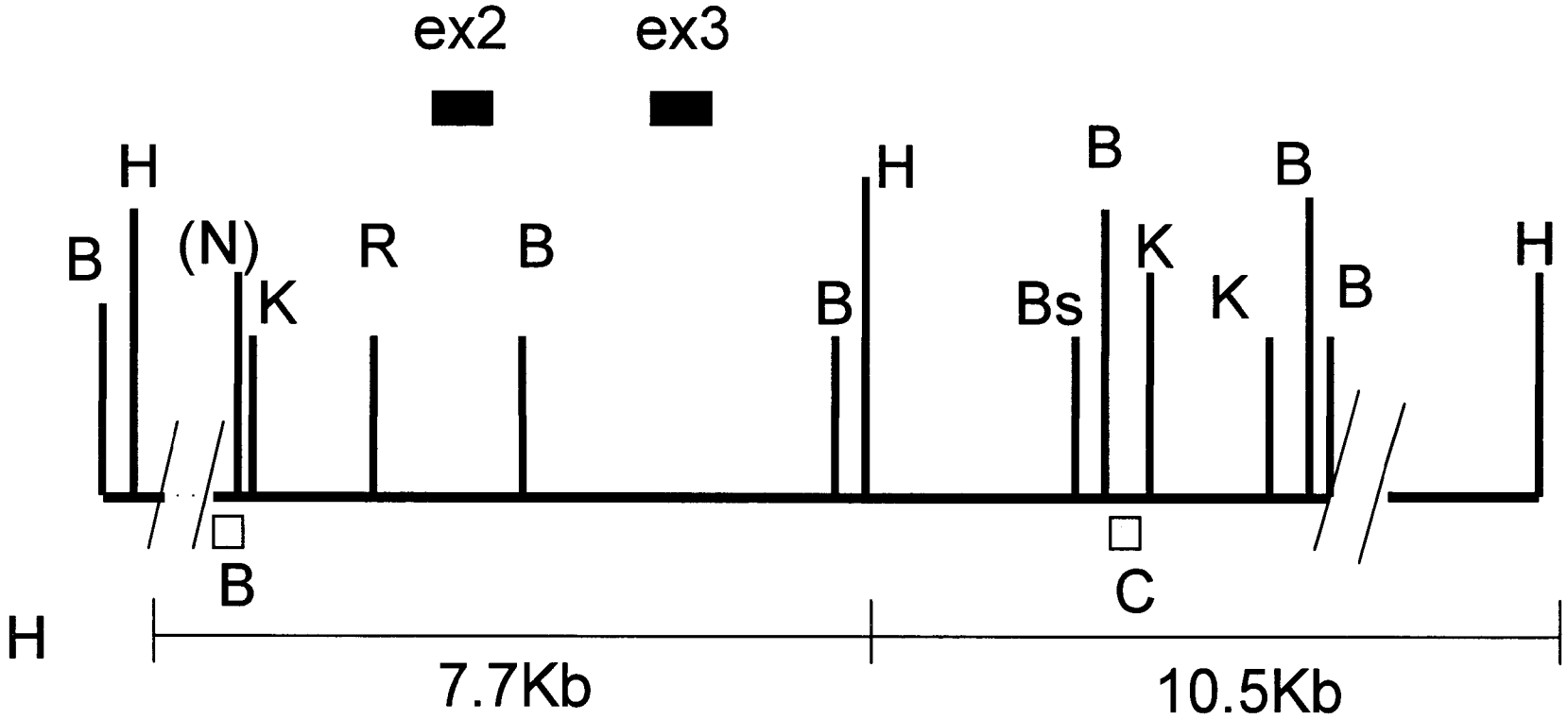

Fig. 3: VHL floxed target allele
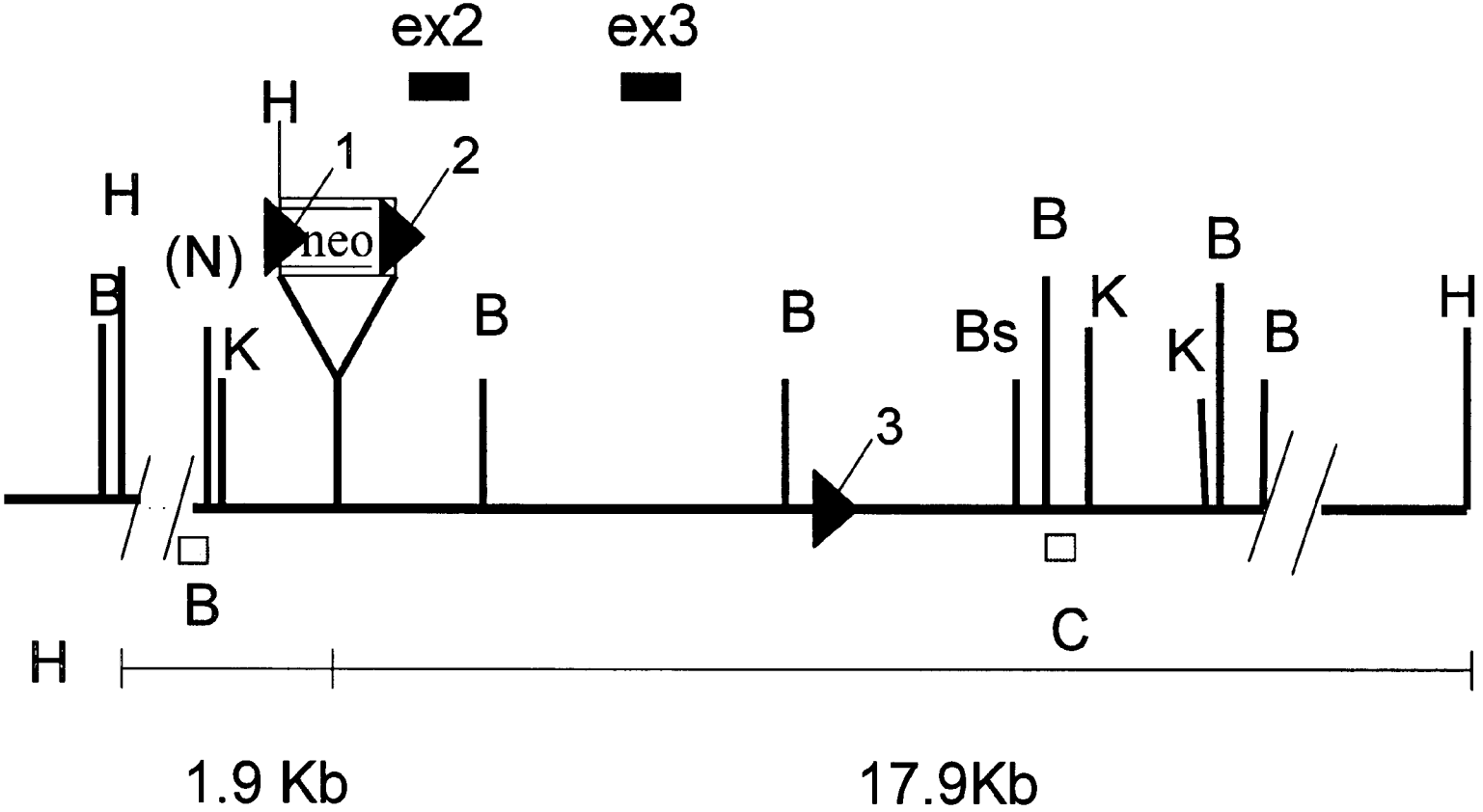

Fig. 4: VHL floxed(-neo) target allele
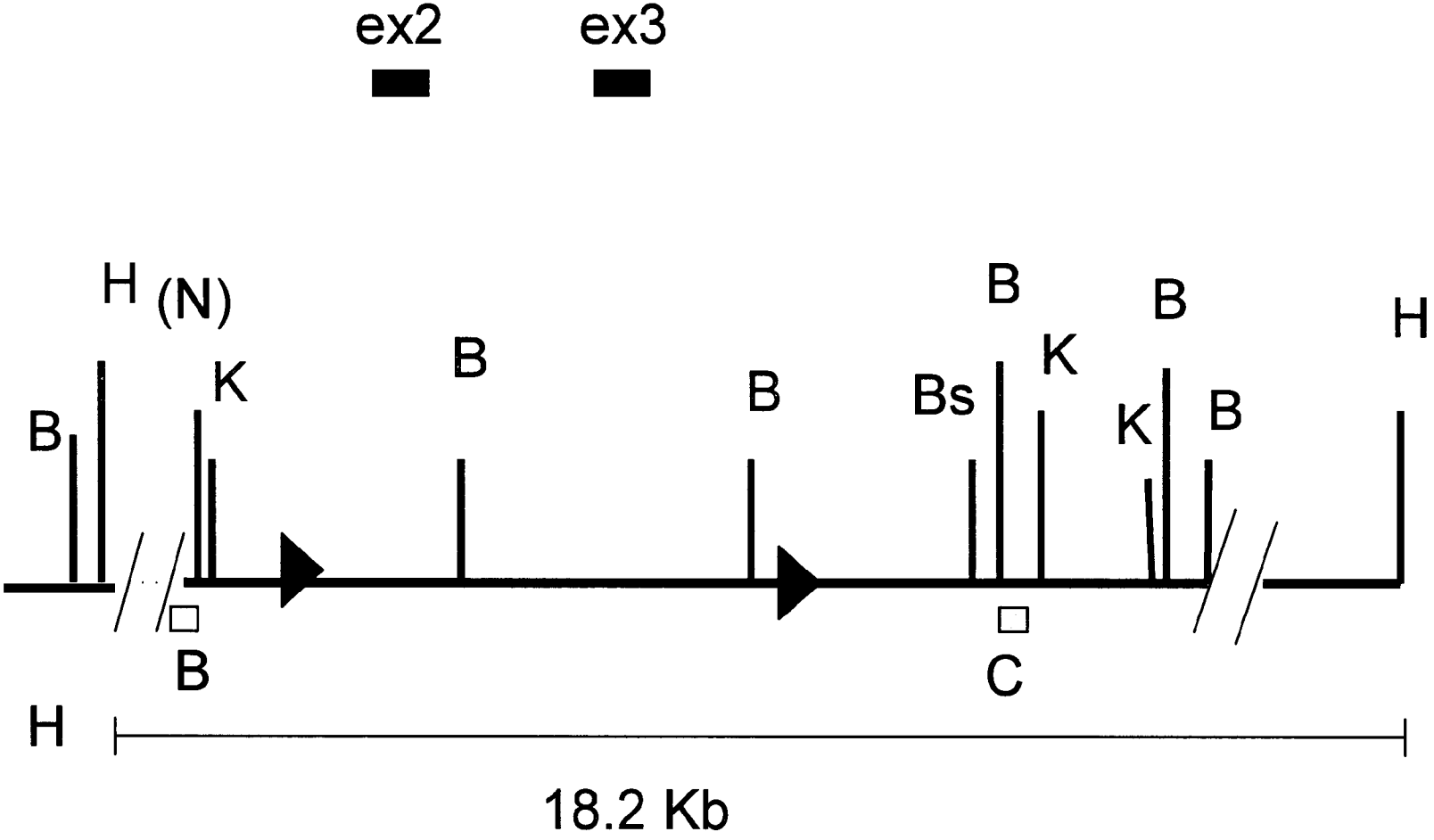

Fig. 5: VHL deleted allele
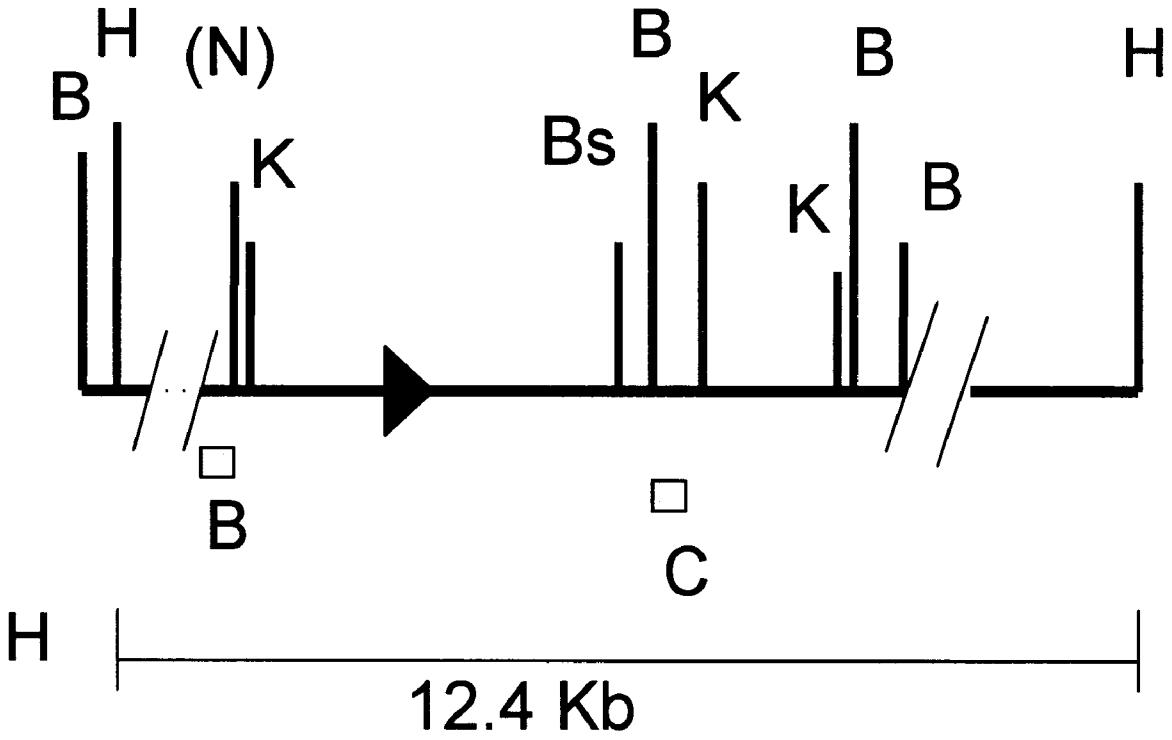

Fig. 6: Mating strategy for VHL conditional knockout mouse model
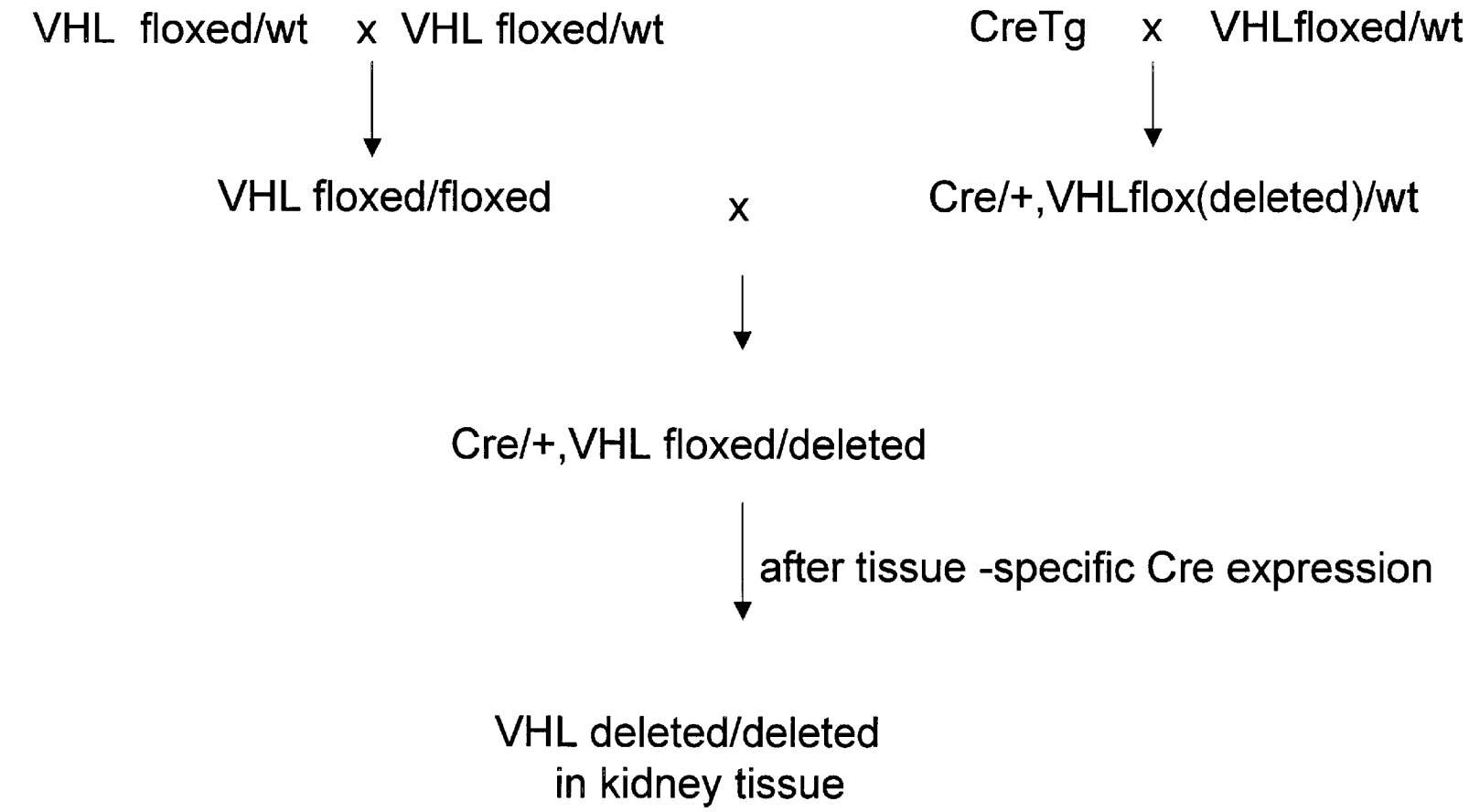

Fig. 7: Southern Hybridization Strategy for Detection of Targeted and Deleted VHL Alleles
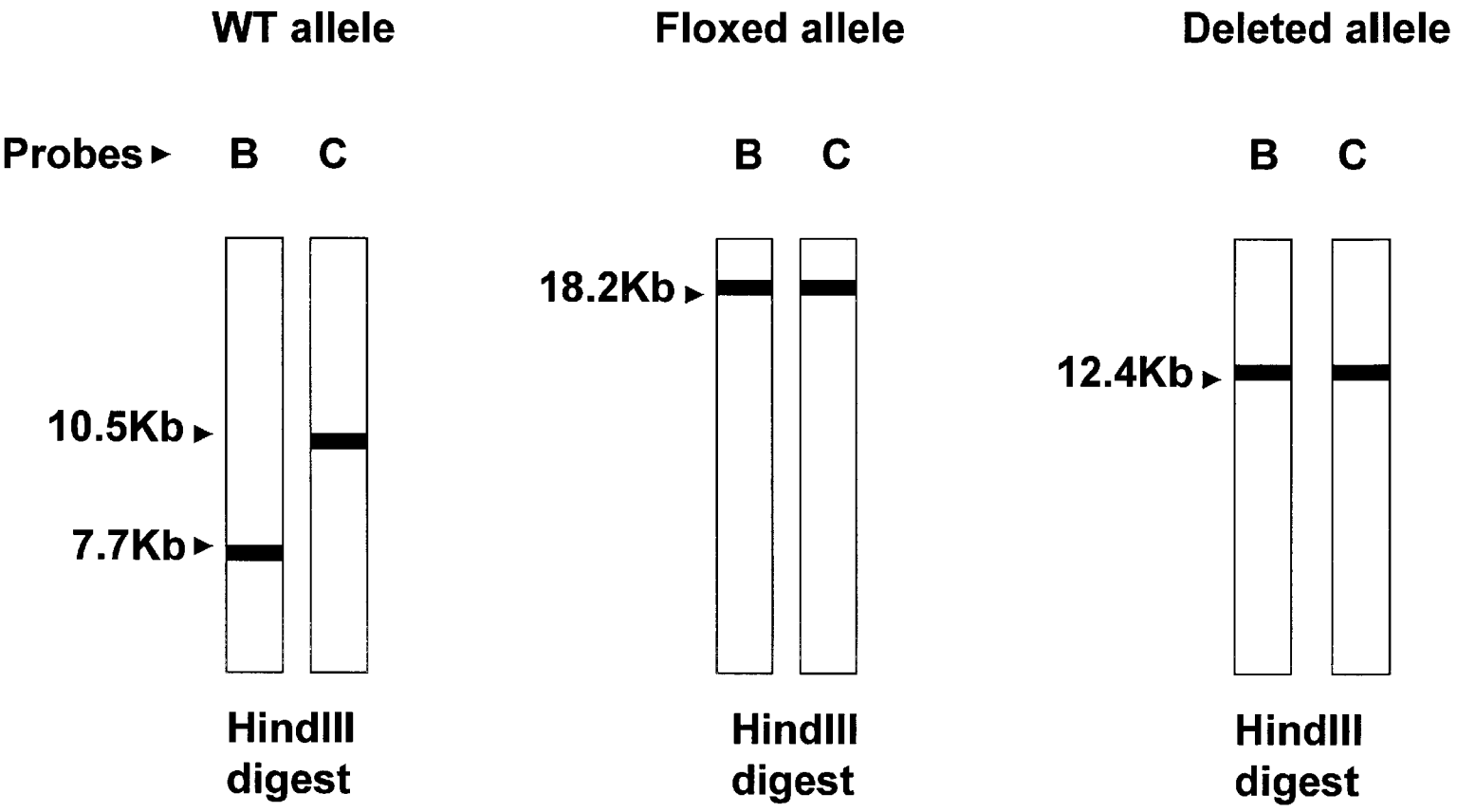

MODEL FOR VON HIPPEL-LINDAU DISEASE

FIELD OF INVENTION

This disclosure relates to nucleic acid molecules that can be used to effect a loss of function of the von Hippel-Lindau (VHL) allele in somatic and/or germ cells of a mammal.

BACKGROUND

Von Hippel-Lindau (VHL) disease is an inherited multisystem disorder characterized by abnormal growth of blood vessels in certain parts of the body, including certain areas of the brain, retina, spinal cord, and adrenal glands. Lesions in the retina can cause retinal detachment and eventual blindness. Cataracts and glaucoma can occur as well. Angiomas in the brain or spinal cord may press on nerve or brain tissue and cause symptoms such as headaches, problems with balance, or weakness of arms and legs. Neurologic symptoms, including seizures and mental retardation, also may be present. However, symptoms vary greatly and depend on the size and location of the growths.

VHL also predisposes individuals to develop tumors of the kidney, adrenal gland, retina, and central nervous system. An autosomal dominant disorder, VHL is the most common form of inherited clear cell renal carcinoma. The multisystem character of the illness, combined with the fact that multiple tumors may form in each target organ, produces considerable morbidity and mortality; the life expectancy of affected individuals is only 49 years (McKusnick, V. A., Mendelian Inheritance in Man (1983) Johns Hopkins University Press. Baltimore and London, p. 534–535).

VHL disease is caused by germline mutations in the VHL tumor suppressor gene on chromosome 3p25. There is a need for a murine model for VHL disease to provide a tool for understanding how inactivation of the VHL gene can lead to the initiation and progression of tumor development in multiple organs. Such an animal model will also serve as a model system for testing tumor regression agents and gene therapies to improve the prognosis and quality of life of VHL patients. Recently, a mouse has been produced with a homozygous VHL gene deletion (Gnarra et al., PNAS 94:9102-9107, 1997). Because that mouse had an embryonic lethal phenotype, it did not provide a model for VHL disease.

SUMMARY OF THE DISCLOSURE

Disclosed herein is a construct that includes at least three recombining sites, the first and second of which flank a selectable marker, and the second and third of which flank an exon of a VHLgene.

In one embodiment, the construct is used to generate a conditional deletion of an exon of a VHL gene. The method for producing the conditional deletion includes targeting the construct via homologous recombination to the endogenous VHL gene in embryonic stem cells, and using these stem cells to produce a conditional VHL targeted animal. In the presence of the appropriate recombinase, the recombining site-flanked portion of the VHL gene is excised. When the recombinase gene is placed under the control of a tissue-specific promoter, expression of the recombinase is directed in a tissue-specific manner and the recombining site-flanked portion of the VHL gene is deleted only in certain tissues.

The foregoing and other features and advantages will become more apparent from the following detailed description of several embodiments, which proceeds with reference to the accompanying figures.

BRIEF DESCRIPTION OF THE FIGURES

FIG. 1 is a schematic diagram of the plasmid vector containing the targeted VHL gene construct.

FIG. 2 is a schematic representation of the VHL wild-type allele with selected restriction sites marked. Two genomic DNA fragments, one of 7.7 Kb and one of 10.5 Kb, are detected by Probes B and C, respectively, when the sequence is digested with the restriction enzyme Hind III. Boxes B and C represent probe binding sites. Key: H=HindIII, B=BamHI, R=EcoRI, K=KpnI, N=NotI, Bs=BssHII, ex2 and ex 3=locations of VHL exon 2 and 3.

FIG. 3 is a schematic representation of the VHL "floxed" target allele. LoxP sites are shown as black triangles 1, 2, and 3. Two fragments, one of 1.9 Kb and one of 17.9 Kb, are detected by Probes B and C, respectively, when the sequence is digested with the restriction enzyme Hind III. These fragment lengths can be used to determine that the construct has been inserted into the wild-type allele. Boxes B and C represent probe binding sites. Key: H=HindIII, B=BamHI, R=EcoRI, K=KpnI, N=NotI, Bs=BssHII, ex 2 and ex 3=locations of VHL exons 2 and 3. The label, neo, indicates the position of the neomycin resistance cassette.

FIG. 4 is a schematic representation of the VHL floxed (-neo) target allele. Transient in vitro expression of an appropriate recombinase causes recombination to occur between recombining sites 1 and 2 (see FIG. 3), retaining one recombining site and removing the neomycin resistance cassette. The two remaining recombination sites are shown as black triangles. An 18.2 Kb HindIII fragment is detected by either probe and can be used to select for ES cells in which the neo cassette is deleted. Boxes B and C represent probe binding sites. Key: H=HindIII, B=BamHI, R=EcoRI, K=KpnI, N=NotI, Bs=BssHII, ex 2 and ex 3=locations of VHL exons 2 and 3..

FIG. 5 is a schematic representation of the VHL deleted allele wherein recombining sites 2 and 3 have recombined. As shown, a 4.0 Kb fragment is obtained when the post-recombination sequence is digested with the restriction enzyme Kpnl). A 12.4 Kb fragment is obtained when the post-recombination sequence is digested with the restriction enzyme Hind III. Boxes B and C represent probe binding sites. Key: H=HindIII, B=BamHI, R=EcoRI, K=Kpnl, N=NotI, Bs=BssHII.

FIG. 6 is a schematic representation of the mating strategy for the VHL conditional knockout mouse model. VHL floxed/wt indicates a mouse that carries one copy of the floxed VHL allele. VHL floxedWVHL floxed indicates a mouse that is homozygous for the VHL floxed allele. Cre Tg indicates a mouse that carries the Cre transgene. Cre/+, VHL flox(deleted)/wt indicates a mouse carrying both the Cre transgene and the VHL floxed allele. In this mouse, the expression of Cre results in recombination occurring at the Lox-P sites, thereby producing the VHL deletion.

FIG. 7 is a schematic of the Southern hybridization strategy for detection of targeted and deleted VHL alleles. The hybridization strategy is also shown on FIGS. 2, 3, 4, and 5.

DETAILED DESCRIPTION

I. Abbreviations

VHL: von Hippel-Lindau

ES: embryonic stem cells

TK: thymidine kinase floxed: flanked by Lox-P sites

II. Terms

Unless otherwise noted, technical terms are used according to conventional usage. Definitions of common terms in molecular biology can be found in Benjamin Lewin, *Genes V,* published by Oxford University Press, 1994 (ISBN 0-19-854287-9); Kendrew et al. (eds.), *The Encyclopedia of Molecular Biology,* published by Blackwell Science Ltd., 1994 (ISBN 0-632-*02182*-9); and Robert A. Meyers (ed.), *Molecular Biology and Biotechnology: a Comprehensive Desk Reference,* published by VCH Publishers, Inc., 1995 (ISBN 1-56081-569-8).

In order to facilitate review of the various embodiments of the disclosure, the following explanations of specific terms are provided:

Animal: Living multicellular vertebrate organisms, a category that includes, for example, mammals, primates, and birds.

Antibiotic Resistance Cassette: A nucleic acid sequence encoding a selectable marker that confers resistance to that antibiotic in a host cell in which the nucleic acid is translated. Examples of antibiotic resistance cassettes include, but are not limited to: kanamycin, ampicillin, tetracycline, chloramphenicol, neomycin, hygromycin, and zeocin.

Antisense, Sense, and Antigene: Double-stranded DNA (dsDNA) has two strands, a 5'->3' strand (plus strand) and a 3'->5' strand (minus strand). Because RNA polymerase adds nucleic acids in a 5'->3' direction, the minus strand of the DNA serves as the template for the RNA during transcription. Thus, the RNA formed will have a sequence complementary to the minus strand, and identical to the plus strand (except that the base uracil is substituted for thymine).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target.

Cancer: Malignant neoplasm that has undergone characteristic anaplasia with loss of differentiation, increased rate of growth, invasion of surrounding tissue, and is capable of metastasis.

Cre: A 38 kD protein that carries out site-specific recombination at unique 34 bp Lox-P sites. Cre belongs to the lambda/integrase family of DNA recombinases, and is similar to Flp recombinase in the types of reactions it carries out, the structure of its target sites, and its mechanism of recombination (Jayaram, *TIBS,* 19:78-82, 1994; Lee et al., *J. Biol. Chem.* 270:4042-52, 1995). The recombination event is independent of replication and exogenous energy sources such as ATP, and functions on both supercoiled and linear DNA templates.

Recombinases exert their effects by promoting recombination between two of their recombining sites. In the case of Cre, the recombining site is a Lox site (see U.S. Pat. No. 4,959,317 to Sauer). These recombining sites are comprised of inverted palindromes separated by an asymmetric sequence (Mack et al. *Nuc. Acids Res.,* 20:4451-5, 1992; Hoess et al., *Nuc. Acids Res.* 14:2287-300, 1986; Kilby et al., *TIG,* 9:413-21, 1993). Recombination between target sites arranged in parallel (so called "direct repeats") on the same linear DNA molecule results in excision of the intervening DNA sequence as a circular molecule. Recombination between direct repeats on a circular DNA molecule excises the intervening DNA and generates two circular molecules. The Cre/Lox recombination system has been used for a wide array of purposes, such as site-specific integration into plant, insect, bacterial, yeast and mammalian chromosomes (Sauer et al., *Proc. Natl. Acad. Sci. USA,* 85, 5166-70, 1988). The use of the recombinant systems or components thereof in transgenic mice, plants and insects, among others, reveals that hosts express recombinase genes with no apparent deleterious effects, thus confirming that the proteins are generally welltolerated (Orbin et a?., *Proc. Natl. Acad. Sci. USA* 89:6861-5, 1992).

Deletion: The removal of a sequence of nucleic acid, such as DNA, the regions on either side being joined together.

DNA (deoxyribonucleic acid): DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine, and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Electroporation: A method of inducing or allowing a cell to take up macromolecules by applying electric fields to reversibly permeabilize the cell walls. Various methods and apparatuses used are further defined and described in: U.S. Pat. No. 4,695,547; U.S. Pat. No. 4,764,473; U.S. Pat. No. 4,882,28; and U.S. Pat. Nos. 4,946,793; 4,906,576; 4,923,814; and 4,849,089.

Eukaryotic cell: A cell having an organized nucleus bounded by a nuclear membrane. These include simpler organisms such as yeasts, slime molds, and the like, as well as cells from multicellular organisms such as invertebrates, vertebrates, and mammals. Multicellular organisms include a variety of cell types, such as: endothelial cell, smooth muscle cell, epithelial cell, hepatocyte, cells of neural crest origin, tumor cell, hematopoetic cell, immunologic cell, T cell, B cell, monocyte, macrophage, dendritic cell, fibroblast, keratinocyte, neuronal cell, glial cell, adipocyte, myoblast, myocyte, chondroblast, chondrocyte, osteoblast, osteocyte, osteoclast, secretory cell, endocrine cell, oocyte, and spermatocyte. These cell types are described in standard histology texts, such as McCormack, Introduction to Histology, (c) 1984 by J. P. Lippincott Co.; Wheater et al., eds., Functional Histology, 2nd Ed., (c) 1987 by Churchill Livingstone; Fawcett et al., eds., Bloom and Fawcett: A Textbook of Histology, (c) 1984 by William and Wilkins.

ES (embryonic stem) cells: Cells derived from the inner cell mass or epiblast of the blastocyst that are capable of undergoing an unlimited number of symmetrical divisions without differentiating. Embryonic stem cells exhibit and maintain a stable, full complement of chromosomes and can give rise to differentiated cell types that are derived from all three primary germ layers of the embryo (endoderm, mesoderm, and ectoderm). They are capable of integrating into all fetal tissues, and mouse ES cells maintained in culture for long periods of time can still generate any tissue when they are reintroduced into an embryo to generate a chimeric animal. ES cells are also capable of colonizing the germ line and giving rise to egg or sperm cells.

ES cells are clonogenic, meaning that a single ES cell can give rise to a colony of genetically identical cells that have the same properties as the original cell. In addition, mouse ES cells express the transcription factor, Oct-4, which activates or inhibits a number of target genes and maintains the ES cells in a proliferative, non-differentiating state, though they can be induced to differentiate.

ES cells lack the Gl checkpoint in the cell cycle; they spend most of their time in the S phase of the cell cycle, during which they synthesize DNA. Unlike differentiated somatic cells, ES cells do not require any external stimulus to initiate DNA replication. In addition, ES cells do not show X inactivation.

Flanked nucleic acid: A nucleic acid sequence flanked at a 5'- and 3'-portion by recombining sites. For example, as shown in FIG. 3, the neomycin resistance cassette is a flanked nucleic acid. In some embodiments, the recombining sites are both Lox-P sites. The flanking recombining sites are generally within 1000 base pairs (bp) of the transcribed region of the flanked target sequence, for example they can be within 500 bp, 200 bp, 100 bp, 50 bp, or 10 bp of the target. The flanking sequences need not be the same distance from the target.

floxed nucleic acid or gene: A nucleic acid sequence, such as a gene, that is flanked on the 5'- and 3'-ends by Lox-P recombining sites.

Foreign gene: Any nucleic acid (e.g., gene sequence) that is introduced into the genome of an animal by experimental manipulations and can include gene sequences found in that animal so long as the introduced gene contains some modification (e.g., a point mutation, the presence of a selectable marker gene, a nonnative regulatory sequence, or a native sequence integrated into the geneome at a nonnative location, etc.) relative to the naturally-occurring gene.

Gene: A DNA sequence that comprises control and coding sequences necessary for the production of a polypeptide or protein. The polypeptide can be encoded by a full-length coding sequence or by any portion of the coding sequence in some embodiments, so long as at least a portion of the desired activity of the polypeptide is retained.

Homologous recombination: An exchange of homologous polynucleotide segments anywhere along a length of two (or more) nucleic acid molecules. Homologous recombination provides a method for introducing a desired gene sequence into a plant or animal cell. Thus, it is capable of producing chimeric or transgenic plants and animals having defined, and specific, gene alterations. A discussion of the process of homologous recombination can be found in Watson, J. D., In: *Molecular Biology of the Gene,* 3rd Ed., W. A. Benjamin, Inc., Menlo Park, Calif. (1977).

In brief, homologous recombination is a well-studied natural cellular process that results in the scission of two nucleic acid molecules having identical or substantially similar sequences (i.e. "homologous"), and the ligation of the two molecules such that one region of each initially present molecule is now ligated to a region of the other initially present molecule (Sedivy, J. M., Bio-Technol. 6:1192-1196 (1988)). Homologous recombination is, thus, a sequence-specific process by which cells can transfer a "region" of DNA from one DNA molecule to another. As used herein, a "region" of DNA is intended to generally refer to any nucleic acid molecule. The region can be of any length from a single base to a substantial fragment of a chromosome.

For homologous recombination to occur between two DNA molecules, the molecules can possess a "region of homology" with respect to one another. Such a region of homology can be at least 1.5 Kb long. Two DNA molecules possess such a "region of homology" when one contains a region whose sequence is so similar to a region in the second molecule that homologous recombination can occur. Recombination is catalyzed by enzymes that are naturally present in both prokaryotic and eukaryotic cells.

Intron: An intragenic nucleic acid sequence in eukaryotes that is not expressed in a mature RNA molecule. Introns of the present disclosure include full-length intron sequences, or a portion thereof, such as a part of a full-length intron sequence.

In vitro amplification: Techniques that increases the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification may be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBATM RNA transcription-free amplification (see U.S. Pat. No. 6,025,134).

Isolated: An isolated biological component (such as a nucleic acid, peptide or protein) has been substantially separated, produced apart from, or purified away from other biological components in the cell of the organism in which the component naturally occurs, i.e. other chromosomal and extrachromosomal DNA and RNA, and proteins. Nucleic acids, peptides and proteins that have been isolated include nucleic acids and proteins purified by standard purification methods. The term also embraces nucleic acids, peptides, and proteins prepared by recombinant expression in a host cell as well as chemically synthesized nucleic acids.

Lox-P sequence: A target recombining site sequence recognized by the bacterial Cre recombinase (Cre). Specific, non-limiting examples include, but are not limited to, the sequence listed as Genbank accession No. M10494.1; LOX P (Genbank Accession No. U51223, herein incorporated by reference); LOX 511 (Bethke and Sauer, *Nuc. Acid. Res.* 25:282-34, 1997); ψLOXh7q21 (Thyagarajan et al., *Gene,* 244:47-54, 2000), ψCoreh7q21 (Thyagarajan et al., *Gene,* 244:47-54, 2000) as well as the Lox sites disclosed in Table 1 of Thyagarajan et al. (*Gene,* 244:47-54, 2000). In one embodiment, LOX P sites are defined by the sequence ATAACTTCGTATAATGTATGCTATACGAAGTTAT (SEQ ID NO 1).

A "minimal" Lox-P sequence is the minimal sequence recognized by Cre. In one embodiment, minimal Lox-P sequence is as described in Hoekstra et al., *Proc. Nat. Acad. Sci.* 88:5457-61, 1991. In one embodiment, 5' and 3' Lox-P sequences are identical.

As used herein, Lox-P sequences are located upstream and downstream (5' and 3', respectively) to a nucleic acid sequence, for example a nucleic acid sequence encoding a transgene, such as a transgene encoding a therapeutic polypeptide, or a marker polypeptide. In another embodiment, the nucleic acid sequence is a stop cassette.

Mammal: This term includes both human and non-human mammals. Similarly, the terms "subject," "patient," and "individual" include human and veterinary subjects.

Neoplasm: Abnormal growth of cells.

Normal cells: Non-tumor, non-malignant cells.

Nucleic acid: A sequence composed of nucleotides, including the nucleotides that are found in DNA and RNA.

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

PCR (polymerase chain reaction): A method of nucleic acid amplification such as that disclosed in U.S. Pat. Nos. 4,683,195, 4,683,202 and 4,965,188, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e. denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g. hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences can be used to obtain segments of DNA (e.g. genes) for the construction of targeting vectors, transgenes, etc.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

Polynucleotide: A linear nucleic acid sequence of any length. Therefore, a polynucleotide includes molecules that are at least 15, 50, 100, 200 (oligonucleotides) and also nucleotides as long as a full-length CDNA.

Probes and primers: A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g. in Sambrook et al., *Molecular Cloning: A Laboratory Manual,* Cold Spring Harbor Laboratory Press (1989); and Ausubel et al., *Current Protocols in Molecular Biology*, Greene Publishing Associates and Wiley-Intersciences (1987).

Primers are short nucleic acids, for example DNA oligonucleotides at least 15 nucleotides in length, and/or no longer than 15, 50, 100 or 200 nucleotides in length. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g. by PCR or other nucleic-acid amplification methods known in the art.

Methods for preparing and using probes and primers are described, for example, in Sambrook et al. (*Molecular Cloning: A Laboratory Manual,* Cold Spring Harbor Laboratory Press, 1989), Ausubel et al., *Current Protocols in Molecular Biology,* Greene Publishing Associates and Wiley-Intersciences (1987), and Innis et al., *PCR Protocols, A Guide to Methods and Applications,* 1990, Innis et al. (eds.), 21–27, Academic Press, Inc., San Diego, Calif. PCR primer pairs can be derived from a known sequence, for example, by using computer programs intended for that purpose such as Primer (Version 0.5, ©1991, Whitehead Institute for Biomedical Research, Cambridge, MA).

Probes and primers disclosed herein comprise at least 15 nucleotides of a nucleic acid sequence, although a shorter nucleic acid can be used as a probe or primer if it specifically hybridizes under stringent conditions with a target nucleic acid by methods well known in the art. The disclosure thus includes isolated nucleic acid molecules that include specified lengths of the disclosed sequences. One of skill in the art will appreciate that the specificity of a particular probe or primer increases with its length. Thus, for example, a primer comprising 20 consecutive nucleotides of a gene will anneal to a target sequence contained within a genomic DNA library with a higher specificity than a corresponding primer of only 15 nucleotides. To enhance specificity, longer probes and primers can be used, for example probes and primers that comprise at least 20, 30, 40, 50, 60, 70, 80, 90, 100 or more consecutive nucleotides from any region of the disclosed sequences. By way of example, the sequences disclosed herein can be apportioned into halves or quarters based on sequence length, and the isolated nucleic acid molecules can be derived from the first or second halves of the molecules, or any of the four quarters.

When referring to a probe or primer, the term "specific for (a target sequence)" indicates that the probe or primer hybridizes under stringent conditions substantially only to the target sequence in a given sample comprising the target sequence.

Prokaryote: Cell or organism lacking a membrane- bound, structurally discrete nucleus and other subcellular compartments.

Promoter: An array of nucleic acid control sequences which direct transcription of a nucleic acid. A promoter includes necessary nucleic acid sequences near the start site of transcription, such as, in the case of a polymerase II type promoter, a TATA element. In one embodiment, a promoter includes an enhancer. In another embodiment, a promoter includes a repressor element. In these embodiments, a chimeric promoter is created (a promoter/enhancer chimera or a promoter/repressor chimera, respectively). Enhancer and repressor elements can be located adjacent to, or distal to the promoter, and can be located as much as several thousand base pairs from the start site of transcription. Examples of promoters that can be used in the present disclosure include, but are not limited to the SV40 promoter, the CMV enhancer-promoter, the CMV enhancer/pactin promoter, and the tissue-specific promoter probasin.

Other promoter sequences that can be used to construct the nucleic acids and practice the methods disclosed herein include, but are not limited to: the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors, any retroviral LTR promoter such as the RSV promoter; inducible promoters, such as the MMTV promoter; the metallothionein promoter; heat shock promoters; the albumin promoter; the histone promoter; the α-actin promoter; TK promoters; B19 parvovirus promoters; the SV10 late promoter; the ApoAI promoter and combinations thereof.

In some embodiments, the promoter is a strong promoter, which promotes transcription of RNA at high levels, for example at levels such that the transcriptional activity of the promoter generally accounts for about 25% of transcriptional activity of all transcription within a cell. The strength of a promoter is often tissue-specific and thus can vary from one cell type to another. For example, CMV is a classic strong promoter because it generates high levels of transcriptional activity in many cell types. Examples of strong promoters include, but are not limited to: CMV; CMV/chicken β-actin; elongation factors 1A and 2A; SV40; RSV; and the MoLV LTR.

In other embodiments, the promoter is a tissue-specific promoter, which promotes transcription in a single cell type or narrow range of tissues. Examples of tissue-specific promoters include, but are not limited to: probasin (which is promotes expression in prostate cells), an immunoglobulin promoter; a whey acidic protein promoter; a casein promoter; glial fibrillary acidic protein promoter; albumin promoter; β-globin promoter; and the MMTV promoter.

In yet other embodiments, the promoter is a hormone-responsive promoter, which promotes transcription only when exposed to a hormone. Examples of hormone-responsive promoters include, but are not limited to: probasin (which is responsive to testosterone and other androgens); MMTV promoter (which is responsive to dexamethazone, estrogen, and androgens); and the whey acidic protein promoter and casein promoter (which are responsive to estrogen).

Purified: The term purified does not require absolute purity; rather, it is intended as a relative term. Thus, for example, a purified protein preparation is one in which the protein is more pure than the protein in its natural environment within a cell. Such proteins may be produced, for example, by standard purification techniques, or by recombinant expression. In some embodiments, a preparation of a protein is purified such that the protein represents at least 50%, for example at least 70%, of the total protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g. by genetic engineering techniques, such as those described in Sambrook et al. (In: *Molecular Cloning: A Laboratory Manual,* Cold Spring Harbor, N.Y., 1989).

Recombining site: A nucleic acid sequence that includes inverted palindromes separated by an asymmetric sequence at which a site-specific recombination reaction can occur. In one specific, non-limiting example, a recombining site is a Lox site, such as Lox P or Lox 511 (see above). In another specific non-limiting example, a recombining site is a Frt site. Frt consists of two inverted 13-base-pair (bp) repeats and an 8-bp spacer that together comprise the minimal Frt site, plus an additional 13-bp repeat that can augment reactivity of the minimal substrate (e.g. see U.S. Pat. No. 5,654,182). In other, specific non-limiting examples, a recombining site is a recombining site from a TN3, a mariner, or a gamma/delta transposon.

Recombinase: A protein which catalyses recombination of recombining sites (reviewed in Kilby et al., *TIG,* 9:413-21, 1993; Landy, *Curr. Opin. Genet. Devel.,* 3:699-707, 1993; Argos et al., *EMBO J.,* 5:433-40, 1986). One specific, non-limiting example of a recombinase is Cre. Another specific, non-limiting example of a recombinase is a Flp protein. Other specific, non-limiting examples of a recombinase are Tn3 recombinase, the recombinase of transposon gamma/delta, and the recombinase from transposon mariner.

The Cre and Flp proteins belong to the lambda/integrase family of DNA recombinases. The Cre and Flp recombinases are similar in the types of reactions they carry out, the structure of their target sites, and their mechanism of recombination (Jayaram, *TIBS,* 19:78-*82, 1994;* Lee et al., *J Biol. Chem.* 270:4042-52, 1995). For instance, the recombination event is independent of replication and exogenous energy sources such as ATP, and functions on both supercoiled and linear DNA templates.

Recombinases exert their effects by promoting recombination between two of their recombining sites. In the case of Cre, the recombining site is a Lox site (see U.S. Pat. No. 4,959,317 to Sauer), and in the case of Flp the recombining site is a Frt site. Similar sites are found in transposon gamma/delta, TN3, and transposon mariner. These recombining sites are comprised of inverted palindromes separated by an asymmetric sequence (Mack et al., *Nuc. Acids Res.,* 20:4451-5, 1992; Hoess et al., *Nuc. Acids Res.* 14:2287-300, 1986; Kilby et al., *TIG,* 9:413-21, 1993). Recombination between target sites arranged in parallel (so-called "direct repeats") on the same linear DNA molecule results in excision of the intervening DNA sequence as a circular molecule. Recombination between direct repeats on a circular DNA molecule excises the intervening DNA and generates two circular molecules. Both the Cre/Lox and flp/frt recombination systems have been used for a wide array of purposes such as site-specific integration into plant, insect, bacterial, yeast and mammalian chromosomes has been reported (Sauer et al., *Proc. Natl. Acad Sci. USA,* 85, 5166-70, 1988). Positive and negative strategies for selecting or screening recombinants have been developed (Sauer et al., *J. Mol. Biol.,* 223, 911-28, 1992). The use of the recombinant systems or components thereof in transgenic mice, plants and insects among others reveals that hosts express the recombinase genes with no apparent deleterious effects, thus confirming that the proteins are generally well-tolerated (Orbin et al., *Proc. Natl. Acad Sci. USA* 89:6861-5, 1992).

Sample: Includes biological samples containing genomic DNA, RNA, or protein obtained from the cells of a subject, such as those present in peripheral blood, urine, saliva, tissue biopsy, surgical specimen, fine needle aspirates, amniocentesis samples and autopsy material.

Selection markers or selectable markers: Refer to the use of a gene that encodes an enzymatic activity that confers resistance to an antibiotic or drug upon the cell in which the selectable marker is expressed. Selectable markers can be "positive"; positive selectable markers typically are dominant selectable markers, i.e. genes that encode an enzymatic activity that can be detected in any mammalian cell or cell line (including ES cells). Examples of dominant selectable markers include, but are not limited to, (1) the bacterial aminoglycoside 3' phosphotransferase gene (also referred to as the neo gene) which confers resistance to the drug G418 in mammalian cells, (2) the bacterial hygromycin G phosphotransferase (hyg) gene which confers resistance to the antibiotic hygromycin and (3) the bacterial xanthine-guanine phosphoribosyl transferase gene (also referred to as the gpt gene) which confers the ability to grow in the presence of mycophenolic acid. Selectable markers can be "negative"; negative selectable markers encode an enzymatic activity whose expression is cytotoxic to the cell when grown in an appropriate selective medium. For example, the HSV-tk gene and the dt gene are commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme. Similarly, the expression of the dt gene selects against cells capable of expressing the Diphtheria toxin. The terms are further defined, and methods further explained, by U.S. Pat. No. 5,464,764.

An animal whose genome "comprises a heterologous selectable marker gene" is an animal whose genome contains a selectable marker gene not naturally found in the animal's genome that is introduced by means of molecular biological methods. A heterologous selectable marker is distinguished from an endogenous gene naturally found in the animal's genome in that expression or activity of the heterologous selectable marker can be selected for or against.

Site-specific recombinase: A recombinase whose activity is limited to DNA of a specific sequence. Examples include the Cre, FLP and FLPE recombinases. Cre recombinases are site-specific for Lox-P recombination sites in a DNA sequence, whereas FLP and FLPE recombinases are site-specific for FRT recombination sites. A recombination site is a nucleic acid sequence specifically recognized by a recombinase. For example, the Cre recombinase specifically binds a Lox-P recombination site, and thereby induces recombination.

Subject: Living multicellular vertebrate organisms, a category that includes both human and veterinary subjects for example, mammals, birds and primates.

Supernatant: The culture medium in which a cell is grown. The culture medium can include material from the cell. If the cell is infected with a virus, the supernatant can include viral particles.

Targeting vector and Targeting construct: Are used interchangeably to refer to oligonucleotide sequences comprising a VHL gene. The term "VHL gene" refers to a gene encoding at least one exon of a VHL sequence. The targeting vector can also comprise a selectable marker gene. In one embodiment, the targeting vector contains genomic sequences flanking exons 2 and 3 of the VHL gene sufficient to permit the homologous recombination of the targeting vector into exons 2 and 3 of the VHL gene resident in the chromosomes of the target or recipient cell (e.g., ES cells). Typically, though not necessarily, the targeting vector contains 2 Kb to 50 Kb of DNA homologous to the VHL gene. In one embodiment, the targeting vector contains 8–20 Kb of DNA homologous to the VHL gene. In another embodiment, the targeting vector contains about 10 Kb of DNA homologous to the VHL gene.

This homologous DNA can be located downstream or upstream of the selectable marker gene, or can be divided on each side of the selectable marker gene. In one embodiment, the selectable marker gene is located upstream of the VHL gene. The targeting vector can contain more than one selectable maker gene. When more than one selectable marker gene is employed, the targeting vector can contain both a positive selectable marker (e.g. the neo gene) and a negative selectable marker (e.g. the Herpes simplex virus tk (HSV-tk) gene). The presence of the positive selectable marker permits the selection of recipient cells containing an integrated copy of the targeting vector whether this integration occurred at the target site or at a random site. The presence of the negative selectable marker permits the identification of recipient cells containing the targeting vector at the targeted site (i.e. which has integrated by virtue of homologous recombination into the target site); cells which survive when grown in medium that selects against the expression of the negative selectable marker do not contain a copy of the negative selectable marker.

The targeting vectors of the present disclosure are of the "replacement-type;" integration of a replacement-type vector results in the insertion of a selectable marker into the target gene. As demonstrated herein, replacement-type targeting vectors can be employed to disrupt a gene by expressing the recombinase, for example as a transgene, resulting in the generation of a null allele (i.e. an allele incapable of expressing a functional protein; null alleles can be generated by deleting a portion of the coding region, deleting the entire gene, introducing an insertion and/or a frameshift mutation, etc.) or can be used to introduce a modification (e.g., one or more point mutations) into a gene.

Transduced and Transformed: A virus or vector transduces or transfects a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transgene: A foreign gene that is placed into an organism by introducing the foreign gene into embryonic stem (ES) cells, newly fertilized eggs or early embryos. In one embodiment, a transgene is a gene sequence, for example a sequence that encodes a marker polypeptide that can be detected using methods known to one of skill in the art. In another embodiment, the transgene encodes a therapeutic polypeptide that can be used to alleviate or relieve a symptom of a disorder. In yet another embodiment, the transgene encodes a therapeutically effective oligonucleotide, for example an antisense oligonucleotide, wherein expression of the oligonucleotide inhibits expression of a target nucleic acid sequence. In a further embodiment, the transgene encodes an antisense nucleic acid or a ribozyme. In yet another embodiment, a transgene is a stop cassette.

In other embodiments, a transgene contains native regulatory sequences operably linked to the transgene (e.g. the wild-type promoter, found operably linked to the gene in a wild-type cell). Alternatively, a heterologous promoter can be operably linked to the transgene. In yet another embodiment, a viral LTR can be used to express the transgene.

Transgenic Cell: Transformed cells that contain foreign, non-native DNA.

Transgenic Animal: An animal, for example, a non-human animal such as a mouse, that has had DNA introduced into one or more of its cells artificially. By way of example, this is commonly done by random integration or by targeted insertion. DNA can be integrated in a random fashion by injecting it into the pronucleus of a fertilized ovum. In this case, the DNA can integrate anywhere in the genome, and multiple copies often integrate in a head-to-tail fashion. There is no need for homology between the injected DNA and the host genome.

Targeted insertion, the other common method of producing transgenic animals, is accomplished by introducing the DNA into embryonic stem (ES) cells and selecting for cells in which the DNA has undergone homologous recombination with matching genomic sequences. For this to occur, there often are several kilobases of homology between the exogenous and genomic DNA, and positive selectable markers are often included. In addition, negative selectable markers are often used to select against cells that have incorporated DNA by non-homologous recombination (random insertion).

VHL gene: Genbank accession number NM_000551, which is incorporated by reference, or any other known VHL gene, including sequences listed in U.S. Pat. No. 5,759,790, as well as sequences from different organisms or fragments, polymorphisms, mutants, or variants thereof.

Vector: A nucleic acid molecule as introduced into a cell, thereby producing a transformed cell. A vector can include nucleic acid sequences that permit it to replicate in the cell, such as an origin of replication. A vector can also include one or more marker or therapeutic transgenes and other genetic elements known in the art.

In some embodiments, the vector is a non-viral vector, such as a bacterial vector. In other embodiments, the vector is a viral vector. Examples of viral vectors include, but are not limited to adenoviral vectors, retroviral vectors, and Herpes viral vectors.

Wild-type: The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e. altered characteristics) when compared to the wild-type gene or gene product. It is noted that naturally-occurring mutants can be isolated; these are typically identified by the fact that they have altered characteristics when compared to the wild-type gene or gene product.

Additional terms commonly used in molecular genetics can be found in Benjamin Lewin, *Genes V* published by Oxford University Press, 1994 (ISBN 0-19854287-9); Kendrew et al (eds.), *The Encyclopedia of Molecular Biology,* published by Blackwell Science Ltd., 1994 (ISBN 0-632-02182-9); and Robert A. Meyers (ed.), *Molecular Biology and Biotechnology: a Comprehensive Desk Reference,* published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprises" means "includes." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

The present disclosure utilizes standard laboratory practices for the cloning, manipulation and sequencing of nucleic acids, purification and analysis of proteins and other molecular biological and biochemical techniques, unless otherwise stipulated. Such techniques are explained in detail in standard laboratory manuals such as Sambrook et al. (In: *Molecular Cloning: A Laboratory Manual,* Cold Spring Harbor, N.Y., 1989), Coffin et al. (*Retroviruses,* Cold Spring Harbor Laboratory Press, 1997) and Ausubel et al., *Current Protocols in Molecular Biology,* Greene Publishing Associates and Wiley-Intersciences (1987). Reviews of standard laboratory procedures for microinjection of heterologous DNAs into mammalian (mouse, pig, rabbit, sheep, goat, cow) fertilized ova include: Hogan et al., *Manipulating the Mouse Embryo,* Cold Spring Harbor Press, 1986; Krimpenfort et al, *Bio/Technology* 9:86, 1991; Palmiter et al., *Cell* 41:343, 1985; Kraemer et al., *Genetic Manipulation of the Early Mammalian Embryo,* Cold Spring Harbor Laboratory Press, 1985; Hammer et al., *Nature,* 315:680, 1985; Purcel et al., *Science,* 244:1281, 1986; Wagner et al., U.S. Pat. No. 5,175,385; Krimpenfort et al., U.S. Pat. No. 5,175,384.

Design of the floxed VHL construct

Disclosed herein are constructs that include at least three recombining sites, two of which flank a selectable marker, and two of which flank at least one exon of a VHL gene (see FIGS. 1 and 3). Recombining sites of use include, but are not limited to, Lox-P, Flp, Tn3 recombinase sites, the recombinase site of transposon gamma/delta, and the recombinase site from transposon mariner.

Selectable markers of use include, but are not limited to, bacterial aminoglycoside 3' phosphotransferase gene (also referred to as the neo gene or neomycin resistance gene), which confers resistance to the drug G418 in mammalian cells; the hprt gene (Littlefield, J. W., *Science* 145:709-710 (1964)); a xanthineguanine phosphoribosyltransferase (gpt) gene; an adenosine phosphoribosyltransferase (aprt) gene (Sambrook et al., In: *Molecular Cloning A Laboratory Manual,* 2nd. Ed., Cold Spring Harbor Laboratory Press, N.Y. (1989)); a tk gene (i.e. thymidine kinase gene), such as the tk gene of herpes simplex virus (Giphart-Gassler, M. et al., *Mutat. Res.* 214:223-232 (1989)); the nptII gene (Thomas, K. R. et al., Cell 51:503-512 (1987); Mansour, S. L. et al., *Nature* 336:348-352 (1988)); and other genes that confer resistance to amino acid or nucleoside analogues, or antibiotics, etc., such as dihydrofolate reductase (DHFR), adenosine deaminase (ADA), asparagine synthetase (AS), hygromycin B phosphotransferase, or a CAD enzyme (carbamyl phosphate synthetase, aspartate transcarbamylase, and dihydroorotase) (Sambrook et al., In: *Molecular Cloning A Laboratory Manual,* 2nd. Ed., Cold Spring Harbor Laboratory Press, N.Y. (1989)).

Alternatively, the selectable marker gene can be any gene that can complement for a recognizable cellular deficiency. For example, the gene for HPRT could be used as the detectable marker gene sequence when employing cells lacking HPRT activity. Alternatively, the presence of the detectable marker sequence in a recipient cell is recognized by hybridization, by detection of radiolabelled nucleotides, or by other assays of detection that do not require the expression of the detectable marker sequence. Such sequences can be detected using in vitro nucleic acid amplification, such as PCR (Mullis, K. et al., *Cold Spring Harbor Symp. Quant. Biol.* 51:263-273 (1986), EP 50,424, EP 84,796, EP 258,017, EP 237,362, EP 201,184,U.S. Pat. No. 4,683,202, U.S. Pat. No. 4,582,788, and U.S. Pat. No. 4,683,194).

The prototypical murine VHL gene is Genbank accession number NM_009507, but any other known VHL gene can be used in the constructs and methods described, including sequences listed in U.S. Pat. No. 5,759,790, as well as sequences from different organisms or fragments, polymorphisms, mutants, or ariants thereof (see, e.g., FIG. 2).

In one embodiment, the first and second of the three recombining sites are adjacent to a selectable marker such that the selectable marker is located between the two recombining sites. In addition, the second and third of the three recombining sites are also adjacent to exons 2 and 3 of a VHL gene, such that exons 2 and 3 of the VHL gene exon are located between two of the recombining sites. Thus, the elements of the construct are aligned as follows: recombining site, selectable marker, recombining site, VHL exon 2, VHL exon 3, recombining site. This sequence of elements can be arranged from 3' to 5' or from 5' to 3' in specific embodiments.

In some embodiments, the recombining sites are Frt sites. Frt consists of two inverted 13-base-pair (bp) repeats and an 8-bp spacer that, together, comprise the minimal Frt site, plus an additional 13-bp repeat that can augment reactivity of the minimal substrate (e.g see U.S. Pat. No. 5,654,182). Frt sites undergo site-specific recombination in the presence of FLP and FLPE recombinases.

In other embodiments, the recombining sites are Lox-P sites. Lox-P is a target recombining site sequence recognized by the bacterial Cre recombinase (Cre). Specific, non-limiting examples of Lox-P sites include the sequence listed as Genbank accession No. M10494.1; LOX P (Genbank Accession No. U51223); LOX 511 (Bethke and Sauer, *Nuc. Acid. Res.* 25:282-34, 1997); ψLOXh7q21 (Thyagarajan et al., *Gene,* 244:47-54, 2000), ψCoreh7q21 (Thyagarajan et al., *Gene,* 244:47-54, 2000) as well as the Lox sites disclosed in Table 1 of Thyagarajan et al. (*Gene,* 244:47-54, 2000).

In certain embodiments, the selectable marker is the bacterial aminoglycoside 3' phosphotransferase gene (also referred to as the neo gene or neomycin resistance gene), which confers resistance to the drug G418 in mammalian cells.

In some embodiments, the construct comprises a floxed VHL allele in which a Lox-P site is inserted into the intron, downstream of exon 3 of the VHL gene and a Lox-P-neo-Lox-P cassette is inserted in the intron upstream of exon 2 of the VHL gene. Additionally, a second selectable marker distinct from the first selectable marker is inserted into the targeting vector sequence (see FIG. 1). In some embodiments, the second selectable marker is a thymidine kinase (TK) gene.

Vectors of Use

The disclosed constructs can be prepared in accordance with conventional methods, where sequences can be synthesized, isolated from natural sources, manipulated, cloned, ligated, subjected to in vitro mutagenesis, primer repair, or the like. At various stages, the joined sequences can be cloned, and analyzed by restriction analysis, sequencing, or the like. Usually the construct will be carried on a cloning vector comprising a replication system functional in a prokaryotic host, e.g., *E. coli,* and a marker for selection, e.g., biocide resistance, complementation to an auxotrophic host, etc. Vectors achieve the basic goal of delivering into the target cell the nucleic acid sequence and control elements needed for transcription. The vector can be a non-viral or viral vector. Vector choice is influenced by the cell in which nucleic acid expression is desired. Other functional sequences can also be present in the vector, such as polylinkers, for ease of introduction and excision of the construct or portions thereof, or the like. A large number of cloning vectors are available and known to those of ordinary skill in the art, such as pBR322, the pUC series, etc. In one embodiment, the construct is carried on a pBluescript vector (Stratagene) (see FIG. 1).

Introduction of the gene sequence into ES cells

The DNA molecule containing the desired gene sequence can be introduced into pluripotent cells (such as ES cells) by any method that will permit the introduced molecule to undergo recombination at its regions of homology. Techniques that can be used include calcium phosphate/DNA co-precipitates, microinjection of DNA into the nucleus, electroporation, bacterial protoplast fusion with intact cells, transfection, polycations, e.g., polybrene, polyornithine, etc. The DNA can be single or double stranded DNA, linear or circular. Techniques for transforming mammalian cells are known, and examples for such methods are described, for instance, in Keown et al., *Meth. Enzym.* (1989), Keown et al., *Meth. Enzym.* (1990) vol. 185, pp. 527–537 and Mansour et al., *Nature,* 336:348-352, (1988).

Some methods, such as direct microinjection, or calcium phosphate transformation, may cause the introduced nucleic acid molecule to form concatemers upon integration. These concatemers can resolve themselves to form nonconcatemeric integration structures. An alternative method for introducing the gene to the pluripotent cell is electroporation (Toneguzzo, F. et al., *Nucleic Acids Res.* 16:5515-5532 (1988); Quillet, A. et al., *J. Immunol.* 141:17-20 (1988); Machy, P. et al., *Proc. Natl. Acad, Sci.* (U.S.A.) 85:8027-8031 (1988)).

After introduction of the DNA molecule(s), the cells are usually cultured under conventional conditions, as are known in the art. A selectable marker (as discussed above) can be used to facilitate the recovery of those cells that have received the DNA molecule containing the desired gene sequence. For the purposes of the present disclosure, any gene sequence whose presence in a cell permits recognition and clonal isolation of the cell can be employed as a detectable marker, whether or not it conveys a survival advantage in the transgenic cell.

After selection for cells that have incorporated the desired DNA molecule, the cells are cultured, and the presence of the introduced DNA molecule is confirmed as described above. For instance, approximately $10^7$ cells are cultured and screened for cells that have undergone a second recombinational event (discussed below), resulting in the replacement of a native sequence (i.e. a gene sequence that is normally and naturally present in the recipient cell) with the desired gene sequence. Any of a variety of methods can be used to identify cells that have undergone the second recombinational event, including direct screening of clones, use of PCR, use of hybridization probes, etc.

In one embodiment, a gene is located upstream or downstream from the targeting construct that provides for identification of whether a double crossover (and therefore targeted integration, not random integration) has occurred. By way of example, the herpes simplex virus thymidine kinase (HSV-tk) gene can be employed for this purpose, since the presence of the thymidine kinase gene is detected by the use of nucleoside analogs, such as acyclovir or gangcyclovir, for their cytotoxic effects on cell that contain a functional HSV-tk gene. The absence of sensitivity to these nucleoside analogs indicates the absence of the thymidine kinase and indicates that, therefore, where homologous recombination has occurred, a double crossover event has also occurred.

Homologous Recombination

Once the DNA molecule containing the construct has been introduced into the ES cells (or other pluripotent cells), the construct recombines with the wild-type VHL gene through the process of homologous recombination. Homologous recombination provides a method for introducing a desired gene sequence into a plant or animal cell and producing chimeric or transgenic plants and animals having defined, and specific, gene alterations. A discussion of the process of homologous recombination can be found in Watson, J. D., In: *Molecular Biology of the Gene,* 3rd Ed., W. A. Benjamin, Inc., Menlo Park, Calif. (1977).

In brief, homologous recombination is a well-studied natural cellular process that results in the scission of two nucleic acid molecules having identical or substantially similar sequences (i.e. "homologous"), and the ligation of the two molecules such that one region of each molecule initially present is now ligated to a region of the other initially present molecule (Sedivy, J. M., *Bio-Technol.* 6:1192-1196 1988). Homologous recombination is a sequence-specific process by which cells can transfer a "region" of DNA from one DNA molecule to another. As used herein, a "region" of DNA is intended to generally refer to any nucleic acid molecule. The region can be of any length from a single base to a substantial fragment of a chromosome, and can, but needs not, include coding regions for one or more proteins.

For homologous recombination to occur between two DNA molecules, the molecules can possess a "region of homology" with respect to one another. Such a region of homology is usually at least two base pairs long, but is more customarily 2–20 Kb long. Two DNA molecules possess such a "region of homology" when one contains a region whose sequence is so similar to a region in the second molecule that base pairing and homologous recombination can occur. Recombination is usually catalyzed by enzymes that are naturally present in both prokaryotic and eukaryotic cells.

The transfer of a region of DNA can be envisioned as occurring through a multi-step process. If either of the two participant nucleic acid molecules is circular, then a recombination event results in the integration of the circular molecule into the other participant nucleic acid molecule. Importantly, if a particular region is flanked on both sides by regions of homology (which can be the same, but can also be different), then two recombinational events can occur, thus resulting in the exchange of a region of DNA between two DNA molecules. Recombination can be "reciprocal," and thus result in an exchange of DNA regions between two recombining DNA molecules. Alternatively, it can be "non-reciprocal" (also referred to as "gene conversion") and result in both recombining nucleic acid molecules having the same nucleotide sequence.

For homologous recombination, constructs are prepared where the gene of interest is flanked on one or both sides with DNA homologous with the DNA of the target region. The homologous DNA is generally within 100 Kb, but can be within 50 Kb, 25 Kb, or, in some embodiments, about 2.5 Kb or 1.5 Kb or more of the target gene. The homologous DNA can include the 5'-upstream region comprising any enhancer sequences, transcriptional initiation sequences, the region 5' of these sequences, or the like. The homologous region can include a portion of the coding region, where the coding region of a gene can include an open reading frame or combination of exons and introns. The homologous region can comprise all or a portion of an intron, where all or a portion of one or more exons also can be present.

Alternatively, the homologous region can comprise the 3'-region, so as to comprise all or a portion of the transcription termination region of a gene, or the region 3' thereof. The homologous regions can extend over all or a portion of a target gene, or be outside the target gene but include all or a portion of the transcriptional regulatory regions of the structural gene. In many embodiments, the homologous sequence will be joined to the gene of interest, proximally or distally. Usually, a sequence other than the wild-type sequence normally associated with the target gene will be used to separate the homologous sequence from the gene of interest on at least one side of the gene of interest. Some portion of the sequence can be the 5' or 3' sequence associated with the gene of interest (the target).

In order to prepare the subject recombining constructs, it is necessary to know the sequence that is targeted for homologous recombination. While a sequence of 14 bases complementary to a sequence in a genome can provide for homologous recombination, normally the individual flanking sequences will be at least about 150 bp, and can be 12 Kb or more, but usually not more than about 8 Kb. The size of the flanking regions are determined by the size of the known sequence, the number of sequences in the genome which can have homology to the site for integration, whether mutagenesis is involved and the extent of separation of the regions for mutagenesis, the particular site for integration, or the like.

Production of Chimeric and Transgenic Animals

Chimeric or transgenic animals are prepared, for example, by introducing a VHL construct as described herein into a precursor pluripotent cell, such as an ES cell, or equivalent, as described above, and in Robertson, E. J., In: *Current Communications in Molecular Biology,* Capecchi, M. R. (ed.), Cold Spring Harbor Press, Cold Spring Harbor, N.Y., 1989, pp. 39–44. The term "precursor" is intended to denote only that the pluripotent cell is a precursor to the desired ("transfected") pluripotent cell that is prepared in accordance with the teachings of the present disclosure. The pluripotent (precursor or transfected) cell can be cultured in vivo, in a manner known in the art (Evans, M. J. et al., *Nature* 292:154-156, 1981) to form a chimeric or transgenic animal.

Any ES cell can be used in accordance with the present disclosure. For instance, in some embodiments, primary isolates of ES cells are used. Such isolates can be obtained directly from embryos such as the CCE cell line disclosed by Robertson, E. J., In: *Current Communications in Molecular Biology,* Capecchi, M. R. (ed.), Cold Spring Harbor Press, Cold Spring Harbor, N.Y. (1989), pp. 39-44), or from the clonal isolation of ES cells from the CCE cell line (Schwartzberg, P. A. et al., *Science* 246:799-803, 1989). Such clonal isolation can be accomplished according to the method of E. J. Robertson (In: *Teratocarcinomas and Embryonic Stem Cells: A Practical Approach,* (E. J. Robertson, Ed.), IRL Press, Oxford, 1987). The purpose of such clonal propagation is to obtain ES cells that have a greater efficiency for differentiating into an animal. Examples of ES cell lines that have been clonally derived from embryos are the ES cell lines, AB1 (hprt+) or AB2.1 (hprt-).

The ES cells can be cultured on stomal cells (such as STO cells (especially SNC4 STO cells) and/or primary embryonic fibroblast cells) as described by E. J. Robertson (In: *Teratocarcinomas and Embryonic Stem Cells: A Practical Approach,* (E. J. Robertson, Ed.), IRL Press, Oxford, 1987, pp 71-112). The stomal (and/or fibroblast) cells serve to eliminate the clonal overgrowth of abnormal ES cells. The cells can be cultured in the presence of leukocyte inhibitory factor ("lif") (Gough, N. M. et al., *Reprod Fertil. Dev.* 1:281-288, 1989; Yamamori, Y. et al., Science 246:1412-1416, 1989). Since the gene encoding lif has been cloned (Gough, N. M. et al., *Reprod Fertil. Dev.* 1:281-288, 1989), it is also possible to transform stomal cells with this gene, by methods known in the art, and to then culture the ES cells on transformed stomal cells that secrete lif into the culture medium.

ES cell lines can be derived or isolated from any species (for example, chicken, etc.), including cells derived or isolated from mammals such as rodents (i.e. mouse, rat, hamster, etc.), rabbits, sheep, goats, fish, pigs, cattle, and primates such as humans.

Transformed ES cells thereafter can be injected into blastocysts. Blastocysts containing the targeted ES cells are implanted into pseudo-pregnant females and allowed to develop to term. The ES cells thereafter colonize the embryo and can contribute to the germ line of the resulting chimeric animal (Jaenisch, *Science,* 240, 1468-1474, 1988). Chimeric offspring are identified, for instance, by coat-color markers, and those showing chimerism are selected for breeding offspring. Those offspring that carry the mutant allele can be identified by coat color or other markers, and the presence of the mutant allele reaffirmed by DNA analysis of blood samples.

The disclosure is illustrated by the following non-limiting Examples:

EXAMPLE 1

Isolation of mouse strain 129 genomic DNA containing the VHL gene

A 129SVJ mouse genomic Lambda phage library was screened with the 1.3 Kb full length mouse VHL cDNA. A phage clone was identified which contained intron 1, exon 2 and exon 3 of the VHL gene, but not exon 1, and the 3'UTR as determined by PCR and Southern analysis using PCR-generated probes for each exon.

The 15 Kb insert was released with a NotI digestion and subcloned into pBluescript vector.

Restriction mapping revealed a unique EcoRi site in intron 1 (upstream of exon 2) and a unique HindIII site downstream of the 3'UTR, useful for insertion of the Lox-P-neo-Lox-P cassette and Lox-P sites, respectively. A unique BssHII site was identified 3' to the HindIII site and on the 5' end, 9.5 Kb from the upstream NotI site. These restriction sites, NotI and BssHII, were utilized to cut and release the 9.5 Kb genomic fragment containing intron 1, VHL exon 2 and exon 3 for subcloning into Bluescript vector (see below).

EXAMPLE 2

Construction of the VHL target vector

An empty pBluescript I vector was digested with EcoRI and HindIII, ends filled in with Klenow enzyme, and blunt end ligated together, to eliminate EcoRI and HindIII sites from the vector (see FIG. 1).

A NotI-BssHII-BamHI adaptor was subcloned into the multiple cloning site (MCS) of NotI/ BamHI cut pBluescript vector to provide a unique BssHII site in the MCS.

The VHL pBluescript plasmid containing the 15 Kb VHL insert derived from the mouse genomic library (Example 1) was digested with Not I and BssHII to release the 9.5 Kb NotI-BssHII insert containing VHL intron 1, exons 2 and 3 and 3'UTR. The 9.5 Kb insert was subcloned into the NotI/BssHII digested pBluescript vector which lacked the EcoRi and HindIII sites. This construct will now be referred to as the VHL target vector.

A Lox-P site was introduced into the unique downstream HindIII site of the VHL target vector, destroying the site, as follows: (a) Two complimentary oligomers were synthesized which, when annealed, generated ds 32 bp Lox-P sequence with overhanging HindIII ends. The $6^{th}$ place of the six-base pair recognition site was changed to destroy the HindIII site. (b) This ds Lox-P oligomer was subcloned into the unique HindIII site in the VHL target vector, destroying the HindIII site.

A Lox-P-neo-Lox-P cassette was introduced into the unique EcoRI site in intron 1 in VHL of this construct as follows: (a) The PMLJ143 vector was obtained from Dr. Lino Tessarollo, Mouse Cancer Genetics Program, NCI-Frederick, which contains the neo resistance gene flanked by Lox-P sites in the following sequence: EcoRI-Lox-P-HindIII-neo gene-Lox-P-BamHI. In order to enable the release of the Lox-P-neo-LoxP cassette by EcoRI, a BamHI-EcoRI-BamHII adaptor was designed and ligated into the 3'BamHI site in the PMLJ143 vector. (b) Digestion with EcoRI released the 1.6 Kb Lox-P-HindIII-neo gene-Lox-P-BamHI insert, which was then subcloned into the EcoRI site of the VHL target vector. A new HindIII site was introduced in this process which is useful for detection of VHL targeted allele vs. VHL wild type allele by Southern analysis of HindIII digested DNA (see diagram of Southern hybridization strategy at bottom of FIGS. 2,3,4,5, as well as FIG. 7). The order of the 5' and 3' Lox-P sites must be in the same orientation, as confirmed by sequencing and restriction enzyme cutting.

A 2.8 Kb insert containing the thymidine kinase gene (for negative selection against random insertion events) was cut from the pGKTK vector (from Dr. Lino Tessarollo) with SalI and ligated into the XhoI site in the MCS of the VHL target vector. FIG. 1 shows the completed VHL target vector.

EXAMPLE 3

Electroporation into Murine ES Cells

DNA Preparation: The VHL target vector as produced in Example 2 was grown in bacteria using standard techniques.

A large-scale digest of this DNA preparation was linearized by digesting the DNA with NotI. The large-scale digest was examined for complete digestion by running 500 ng on a minigel. The DNA concentration of the large-scale digest should be no higher than 1 μg/μl.

The large-scale digest was extracted twice with an equal volume of phenol and twice with an equal volume of chloroform. The DNA was precipitated with 2.4 volumes of ethanol, pelleted by centrifugation, and air-dried briefly.

The pelleted DNA then resuspended at the desired concentration (usually 1 μg/μl) in a sterile water (20 μl of DNA per electroporation). The concentration of the DNA was then measured with a spectrophotometer and used for electroporation.

Preparation of Cells for Electroporation: Embryonic stem cells of the AB1 cell line were cultured to approximately 80% confluence according to the methods of E. J. Robertson (In: *Teratocarcinomas and Embryonic Stem Cells: A practical Approach,* (E. J. Robertson, Ed.), IRL Press, Oxford, 1987, pp 71-112). Cells were cultured in the presence of stomal cells that expressed lif into the culture medium. Cells were passaged the day before electroporation, and fed 4 hours before harvesting with DMEM, 15% FCS, antibiotics, MEM non-essential amino acids and LIF at 500–1000Unit/ml.

Cells were harvested by trypsinizing the cells, then resuspending them in ES cell media (cells from 2×10 cm plates were combined in a total volume of 10 ml in a 15 ml tube).

The cells were pelleted by centrifugation, and the supernatant was removed by aspiration. The cells were then resuspended in 10 ml of commercially available phosphate buffered saline, pH 7.3, and the total number of cells determined by counting the cells in a 20 μl aliquot. The yield was customarily $30\times10^6$ cells per 10 cm plate.

The cells were then pelleted by centrifugation and the supernatant was removed by aspiration. Cells were resuspended at a density of $11\times10^6$ cells/ml. A 20 μl aliquot was counted to confirm this cell density.

Electroporation: Cells, prepared as described above, were incubated in the presence of 20 μg of linear plasmid DNA in a 15 ml tube. 20μl of DNA (1μg/ml) and 0.8 ml of cells were used for each electroporation.

The mixture was allowed to incubate at room temperature for 5 minutes (this step can, however, be omitted). The cell/DNA mixture was then carefully aliquoted into electroporation cuvettes (0.9 ml per cuvette). The cuvette was placed in the electroporation holder with the foil electrodes of the electroporation device in contact with the metal holding clips.

Electroporation was accomplished using a Biorad GenePulser set at 250 V, 500 μF (this requires a capacitance extender). Optimal transformation was achieved with a time constant of between 5.6 and 7.0.

The cuvette was left at room temperature for 5 minutes and then the cells were plated at an appropriate density (up to $2\times10^7$ cells/100 mm plate or $6\times10^6$ cells/60 mm plate). When G418 was used as a selective agent, this cell density should not be exceeded since G418 takes 3–4 days before killing starts and plates will become overconfluent if the original plating density is too high. G418 selection, when used, was applied 24 hours post-electroporation. G418 concentration, approximately 250 μg/ml, can be titrated for every batch of cells.

The plate(s) were re-fed with fresh media+G418 every day for the first 6–7 days (until colonies are visible and most cell debris has been removed). If using FIAU (0.2μM) selection, this can proceed simultaneously with G418 selection.

Colonies can be picked as early as 8 days, or can be picked at around 10–11 days. Colonies can, however, be recovered up to 18–21 days after the electroporation.

EXAMPLE 4

Selection of ES cells containing the VHL target allele

The final VHL target vector contained 1.4 Kb of homology at the 5' end and 2.5 Kb of homology at the 3'end. The vector was linearized with NotI and electroporated into pluripotent mouse strain 129 embryonic stem cells using the procedures described in Example 3.

Homologous recombinants, in which the wild type VHL genomic sequence was replaced by the VHL target allele containing the neo cassette, were selected by their resistance to G418 (300 μg/ml) in the growth medium. Negative selection against random integration of the vector (and retention of the TK gene) was ensured by maintaining gancyclovir (2 μM) in the medium. Cells that express the TK gene metabolize this chemical and die.

Southern analysis of HindIII digested ES cell DNA using 5' and 3' external DNA probes was used to detect ES cells that contained the VHL target allele. The 5' probe (B) detected a 7.7 Kb HindIII fragment for the wild type VHL allele and a 1.9 Kb HindIII fragment for the VHL targeted allele containing the neo cassette with the new Hind III site. Probe B is a 250 bp PCR product amplified from the mouse VHL cDNA using the following primers: forward primer: CTC-AGG-TGT-ACA-ATCCCC-AG; reverse primer: GAC-ACA-ATC-TTG-GGG-CTT-AGC. The 3'probe (C) detected a 10.5 Kb HindIII fragment for the wild type allele and a 17.9 Kb fragment for the targeted allele. Probe C is a 250 bp PCR product amplified from mouse VHL cDNA using the following primers: forward primer: CAT-ATG-AGA-GCA-CTG-GAG-TCC; reverse primer: ACA-TGC-TTG-TGG-ATC-CTT-TGG-CC.

It was desirable to eliminate the neo cassette before putting the targeted ES cells into mice. Correctly targeted ES cells were transfected with a plasmid carrying the Cre recombinase, and then grown up and plated out at a single cell density. Replica plates were made onto media with and without G418 and clones that were no longer resistant to the chemical, indicating they had lost the neo gene, were selected . DNA was prepared from G418 sensitive clones and analyzed by Southern analysis for HindIII fragment size. If the neo cassette flanked by Lox-P sites had been eliminated by Cre recombination, the new HindIII site within the cassette was also lost. Both the 5' and 3' probes detected a new HindIII fragment size of 18.2 Kb in ES cells containing the VHL target allele minus the neo cassette (FIG. 4).

EXAMPLE 5

Production of VHL flox/+ mice, VHL deleted/+, Cre/+ mice and VHLflox/deleted, Cre/+ mice The VHL targeted ES cells were injected into C57BL/6 blastocysts and carried to term in pseudopregnant females.

Chimeric offspring with >70% agouti coat color were evaluated for germline transmission of the VHL target floxed allele by Southern analysis of tail DNA as described above for ES cells in Example 4.

Brother/sister mating of the selected offspring produced VHL flox/flox mice (FIG. 6).

Mating of VHL flox/+ mice with transgenic mice carrying the Cre recombinase under a tissue specific promoter produced mice carrying one VHL floxed allele and the Cre gene as a transgene. In these mice, Cre deleted the VHL floxed allele in a tissue specific manner.

Mating of the VHL flox/flox mice with VHL deleted/+ mice carrying the Cre transgene produced mice with a VHL flox/deleted genotype carrying the Cre recombinase. These mice should show homozygous deletion of the VHL gene in a tissue specific manner and are expected to produce a tumor phenotype.

It will be apparent that the precise details of the methods described can be varied or modified without departing from the spirit of the disclosure. We claim all such modifications and variations that fall within the scope and spirit of the claims below.

We claim:

1. A nucleic acid molecule comprising:

a first, second, and third Lox-P site, a neomycin resistance cassette flanked by the first and the second Lox-P sites, and exons 2 and 3 of a VHL gene flanked by the second and the third Lox-P sites.

* * * * *